Figure 1:
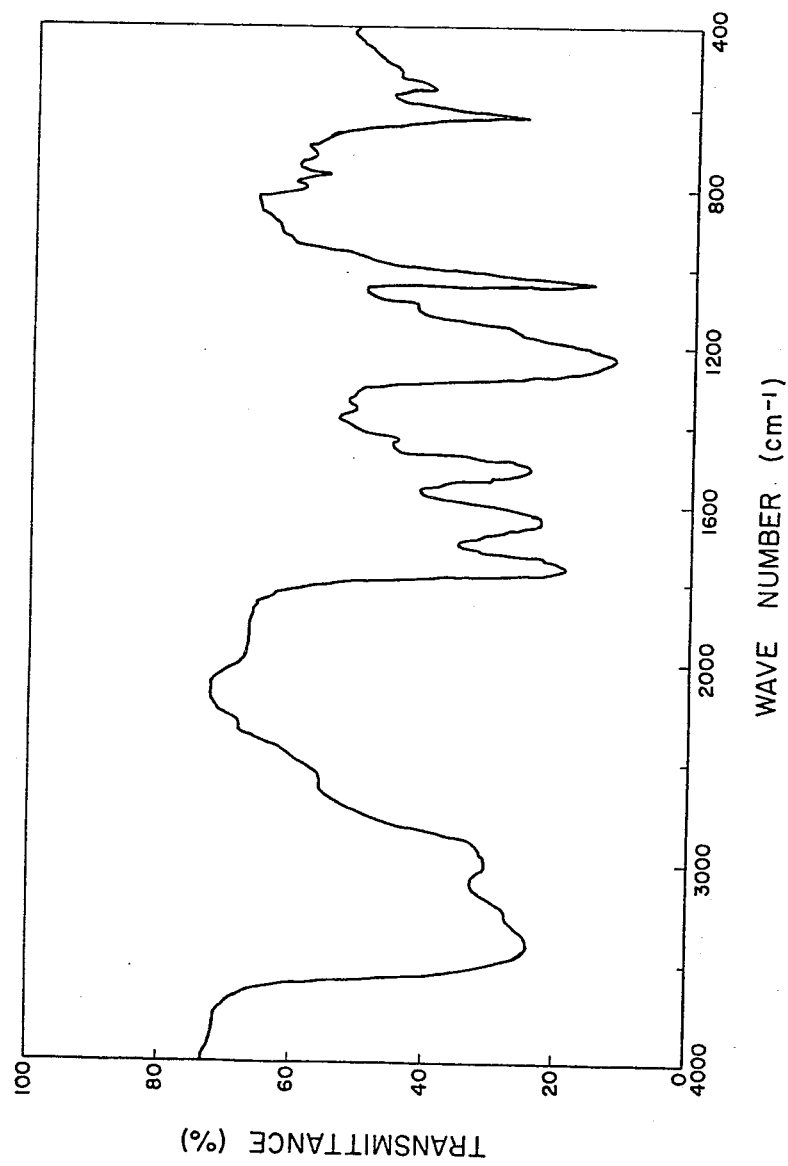

| United States Patent [19] | [11] | 4,225,586 |
|---|---|---|
| Imada et al. | [45] | Sep. 30, 1980 |

[54] ANTIBIOTIC SB-72310

[75] Inventors: Akira Imada, Nishinomiya; Kazuhiko Kintaka, Takatsuki; Konomi Haibara, Osaka, all of Japan

[73] Assignee: Takeda Chemical Industries, Ltd., Osaka, Japan

[21] Appl. No.: 971,090

[22] Filed: Dec. 15, 1978

[30] Foreign Application Priority Data

Oct. 3, 1978 [JP] Japan ................ 53/122277

[51] Int. Cl.$^2$ ............................................. A61K 35/00
[52] U.S. Cl. ...................................... 424/117; 435/170
[58] Field of Search ................ 424/117; 195/80 R; 435/170

[56] References Cited

U.S. PATENT DOCUMENTS 4,031,206   6/1977   Celmer et al. .................. 424/117

Primary Examiner—Jerome D. Goldberg
Attorney, Agent, or Firm—Wenderoth, Lind & Ponack

[57] ABSTRACT

A novel Antibiotic SB-72310 is produced by cultivating a microorganism belonging to the genus Pseudomonas and being capable of producing Antibiotic SB-72310 in a culture medium to have Antibiotic SB-72310 elaborated and accumulated in the cultured broth and recovering the antibiotic.

Antibiotic SB-72310 is useful as a germicide or disinfectant.

3 Claims, 2 Drawing Figures

ANTIBIOTIC SB-72310

This invention relates to Antibiotic SB-72310, salts thereof and a method for producing them.

For the purpose of finding new antibiotics, we isolated a large number of microorganisms from soil samples and investigated the antibiotics which such microorganisms produced. The investigation showed that some of those microorganisms would elaborate a novel antibiotic, that those microorganisms belong to the genus Pseudomonas and that, on cultivation in a suitable culture medium, those microorganisms would accumulate an antibiotic which is inhibitory to gram-positive and gram-negative bacteria. We isolated this antibiotic and, based on its physicochemical and biological properties, established that this antibiotic is a new antibiotic. We accordingly designated it Antibiotic SB-72310.

The conditions for production of Antibiotic SB-72310 were also studied and it was discovered that the production of Antibiotic SB-72310 could be significantly increased by growing any of those microorganisms in a culture medium supplemented with a sulfur compound which the microorganism is able to utilize. These findings were followed by further research which culminated in the present invention.

Throughout this specification and the claims forming parts of this application, Antibiotic SB-72310 will sometimes be referred to briefly as SB-72310.

This invention is directed to:
(1) Antibiotic SB-72310 and salts thereof; and
(2) A method for producing Antibiotic SB-72310 characterized by cultivating a microorganism which belongs to the genus Pseudomonas and is capable of producing Antibiotic SB-72310 in a culture medium to have Antibiotic SB-72310 elaborated and accumulated in the cultured broth and recovering the antibiotic.

The Antibiotic SB-72310-producing strain employed in accordance with this invention may be any bacterial strain of the genus Pseudomonas only if it is able to elaborate Antibiotic SB-72310. As an example of such strain, there may be mentioned Pseudomonas Strain SB-72310 (hereinafter referred to sometimes as Strain SB-72310 which we isolated from soil samples collected in Nishinomiya, Hyogo Prefecture, Japan.

The bacteriological characteristics of Pseudomonas Strain SB-72310 are as follows.

(a) Morphology:

After 2 days on a nutrient-agar slant at 28° C., the cells are rod-shaped, 0.8 to 1.1μ in diameter and 1.6 to 4.1μ long. Without polymorphism, motile with polar flagella or a polar flagellum. Non-sporulating; poly-beta-hydroxybutyric acid is accumulated as an intra-cellular carbon reserve (R. Y. Stanier et al: Journal of General Microbiology 43, 159(1966)). Gram-negative, non-acid-fast.

(b) Cultural characteristics on various media:
Grown at 28° C. and observed for 1 to 14 days.
(1) Nutrient agar plate: Circular, raised colonies of 1 to 3 mm diameter with entire margins are formed after 3 days; smooth; opaque; gray white; no diffusible pigment produced.
(2) Nutrient agar slant: Moderate growth, filiform, opaque and gray.
(3) Nutrient broth: Turbid growth, substantially with a small amount of sedimentation. A pellicle appears.
(4) Nutrient gelatin stab: Liquefaction.
(5) Litmus milk: Peptonization (c) Physiological characteristics
(1) Reduction of nitrates: Positive
(2) Denitrification: Negative
(3) MR (methyl red) test: Negative
(4) VP (Voges-Proskauer) test: Negative
(5) Production of indole: Negative
(6) Production of hydrogen sulfide: Negative
(7) Hydrolysis of starch: Negative
(8) Utilization of citrate: Positive
(9) Utilization of inorganic nitrogen sources
  (I) Potassium nitrate: Positive
  (II) Ammonium sulfate: Positive
(10) Production of pigments: None
(11) Urease: Positive
(12) Oxidase: Positive
(13) Catalase: Positive
(14) Range of growth
  (I) pH: Growth at pH 4.0 to 8.85, optimal pH 4.5–7.0
  (II) Temperature: Growth at 8° to 42° C., optimal 24° to 36° C.
(15) Oxygen demand: Aerobic
(16) O-F (oxidative-fermentative) test [Hugh-Leifson method]: Oxidative
(17) Production of acid and gas from sugars: Weak acid production but no gas production is noted in peptone-water containing 1 W/V% of L-arabinose, D-xylose, D-glucose, D-mannose, D-fructose, D-galactose, maltose, sucrose, trehalose, D-sorbitol, D-mannitol, inositol or glycerol.
(18) Assimilation of carbon sources: The results of cultivation in inorganic salt media (dipotassium hydrogen phosphate 0.7 W/V%, monopotassium dihydrogen phosphate, 0.3 W/V%, ammonium sulfate 0.1 W/V%, sodium chloride 0.1 W/V%, magnesium sulfate.7$H_2O$ 0.01 W/V%) containing various carbon sources for 14 days are given in Table 1.

TABLE 1

Assimilation of Carbon Sources

| Carbon source | Final concentration (W/V %) | Growth |
|---|---|---|
| L-Arabinose | 1 | + |
| D-Xylose | 1 | + |
| D-Glucose | 1 | + |
| D-Mannose | 1 | + |
| D-Fructose | 1 | + |
| D-Galactose | 1 | + |
| Maltose | 1 | + |
| Sucrose | 1 | + |
| Lactose | 1 | − |
| Trehalose | 1 | + |
| D-Sorbitol | 1 | + |
| D-Mannitol | 1 | + |
| Inositol | 1 | + |
| Glycerol | 1 | + |
| Starch | 1 | − |
| Raffinose | 1 | + |
| Citrate | 0.3 | + |
| Acetate | 0.3 | + |
| L-Alanine | 0.3 | + |
| β-Alanine | 0.3 | + |
| Succinate | 0.3 | + |
| 2-Ketogluconate | 0.3 | + |
| L-Arginine | 0.3 | + |
| Betaine | 0.3 | + |

Notes:
+ Growth
± Scant growth
− No growth

(19) Other properties
  (I) Utilization of malonate: Positive (II) Deamination of phenylalanine: Negative
(III) Decarboxylase activity
  (a) Arginine: Positive
  (b) Lysine: Negative
  (c) Ornithine: Negative
(IV) Arginine dehydrolase activity: Positive
(V) Hydrolysis of esculin: Positive
(VI) Hydrolysis of Tween 80: Positive
(VII) The GC (guanine-cytosine) content of DNA: 64.3 mol %

Comparison of the above bacteriological characteristics of Strain SB-72310 with the description in Bergey's Manual of Determinative Bacteriology, Ed. 7 & 8, shows that, in view of its being a gram-negative rod-shaped aerobic bacterium motile with polar flagella or a polar flagellum, oxidase-positive and catalase-positive, Strain SB-72310 obviously belongs to the family Pseudomonadaceae.

The fact that it has no nutritional requirements, accumulates poly-$\beta$-hydroxybutyrate as an intracellular carbon reserve and utilizes arginine or betaine as a single carbon source suggests that the strain is relatively akin to *Pseudomonas pseudoalcaligenes, Pseudomonas pseudomallei, Pseudomonas mallei* or *Pseudomonas caryophylli*. The strain SB-72310, however, differs from those species from the following standpoints: *Pseudomonas pseudoalcaligenes* can use only fructose as a carbon source. Most strains of *Pseudomonas pseudomallei* causes denitrification, hydrolyses starch and have a specific assimilation of nutritive sources *Pseudomonas mallei* is not motile and causes denitrification. *Pseudomonas caryophylli* produces yellow green non-fluorescent pigment and causes denitrification.

Therefore, Strain SB-72310 is considered to belong to a new species of the genus Pseudomonas. And in view of the feature that its low optimal growth pH is 4.5 to 7.0, which is somewhat low for bacteria of the genus Pseudomonas generally, Strain SB-72310 was named *Pseudomonas mesoacidophila* SB-72310.

Samples of this Strain SB-72310 have been respectively deposited at the Fermentation Research Institute, Agency of Industrial Science and Technology (FERM), Chiba, Japan under the receipt number of 4653, at Institute for Fermentation, Osaka (IFO), Japan under the accession number of IFO 13884 and at the American Type Culture Collection (ATCC), Maryland, U.S.A. under the accession number of ATCC-31433.

The Pseudomonas bacteria employed in accordance with this invention generally are highly variable in characteristics and undergo mutation readily when subjected to artificial mutagenic treatments such as irradiation with ultraviolet light or X-rays or treatment with chemical mutagens (e.g. nitrosoguanidine, ethylmethane sulfonate). However, any and all of such mutants and variants are useful for the purposes of this invention only if they possess and retain the ability to elaborate SB-72310, the subject antibiotic of this invention. For the cultivation of Strain SB-72310, there may be employed such carbon sources as glucose, sucrose, maltose, spent molasses, glycerol, oils and fats (e.g. soybean oil, olive oil, etc.), organic acids (e.g. citric acid, succinic acid, gluconic acid, etc.) and other assimilable carbon sources. As nitrogen sources there may be employed organic and inorganic nitrogen-containing compounds and materials such as, for example, soybean flour, cottonseed flour, corn steep liquor, dried yeast, yeast extract, meat extract, peptone, urea, ammonium sulfate, ammonium nitrate, ammonium chloride, ammonium phosphate, etc. Moreover, the inorganic salts normally required for cultivation of bacteria, such as sodium chloride, potassium chloride, calcium carbonate, magnesium sulfate, monopotassium dihydrogen phosphate, disodium monohydrogen phosphate, etc., may be employed either alone or in a suitable combination. It has been found that the yield of the desired antibiotic can be increased by supplementing such a medium with a sulfur compound which the SB-72310 producer is able to utilize, viz. inorganic sulfur compounds such as sulfates (e.g. ammonium sulfate), thiosulfates (e.g. ammonium thiosulfate), sulfite (e.g. ammonium sulfite), etc. or organic sulfur compounds such as sulfur-containing amino acids (e.g. cystine, cysteine, L-thiazolidine-4-carboxylic acid), hypotaurine, sulfur-containing peptide (e.g. glutathione), or a mixture thereof. The concentration of such sulfur compounds in the culture medium is 0.01 to 1.0 W/V percent and, preferably, 0.02 to 0.5 W/V percent. Addition of such a sulfur compound to the medium results in an increased production of SB-72310, thus being commercially of considerable value.

In addition, salts of heavy metals such as ferrous sulfate, copper sulfate, etc., vitamins such as vitamin $B_1$, biotin, etc. and other additives may be incorporated as required. Antifoams and surfactants such as silicone oil, polyalkylene glycol ether, etc. may also be added. Of course, other organic or inorganic matters which would assist in growth of the microorganism and promote production of SB-72310 may also be added in suitable amounts. The cultivation of Strain SB-72310 may be conducted by procedures similar to those used for the production of antibiotics in general, employing a solid culture of a liquid culture method. In the case of liquid culture, it may be stationary, stirring, shaking or aerobic, although aerobic stirring culture is particularly desirable. The preferred cultivation temperature range is about 15° to 35° C., while the pH of the culture medium may range from about 4 to 8. The cultivation is continued for about 8 to 168 hours, preferably for 24 to 144 hours. Since the product Antibiotic SB-72310 is for the most part present in the liquid phase of the fermentation broth, it is advantageous to centrifuge or filter the broth to separate supernatant fluid or filtrate from a cellular mass and purify SB-72310 in the supernatant fluid or filtrate. However, direct purification from the fermentation broth is also feasible, if desired.

Assay of the potency of the product thus obtained may be performed against *Comamonas terrigena* IFO 12685 as the test organism and using SB-72310 as the standard by the cylinder method or paper disk method employing TSA [trypticase soy agar (Baltimore Biologicals, Laboratories, U.S.A.)].

Antibiotic SB-72310 may be recovered by means of the various procedures commonly employed for the recovery of microbial metabolites. Thus, for example, the cells are removed by centrifugation and the active product is separated from the supernatant fluid and purified by the conventional methods. For example, the procedure which makes use of the solubility or solubility difference with respect to a suitable solvent, the procedure utilizing the precipitation or difference in the rates of precipitation of the antibiotic from a solution, the procedure which utilizes its characteristic absorptive affinity for various adsorbents, ion exchange chromatography on ion-exchangers, concentration under reduced pressure, freeze-drying, crystallization, recrystallization, drying, etc. may be utilized either singly or in a suitable combination and sequence and/or in repetition.

A typical procedure may be described below. Thus, after the cultivation has been completed, the fermentation broth is filtered, the resultant filtrate is passed through a column of activated charcoal and the adsorbed SB-72310 is eluted with a hydrophilic organic solvent. As examples of the hydrophilic organic solvent there may be mentioned lower ketones (e.g. acetone, methyl ethyl ketone, methyl isobutyl ketone, etc.), lower alcohols (e.g. methanol, ethanol, isopropanol, propanol, butanol, etc.). These solvents may be used alone or as a mixture in combination with water. Because of the acidic nature of the SB-72310, anion exchange resin such as Cl-form resins [Amberlite IRA-400 & 402, manufactured by Amberlite Co., U.S.A.; Dowex-1, Dow and Chemical Co., U.S.A.; Diaion SA-21A, Mitsubishi Chemical Industries, Ltd., Japan] can be employed with advantage. The adsorbed active product is eluted, for example with an aqueous solution of sodium chloride. To desalt the eluate, column chromatography is carried out again with activated charcoal. The eluate obtained is then concentrated, acetone, for instance, is added and the resultant precipitate is recovered by filtration, washed with acetone, diethyl ether or the like and dried under reduced pressure to recover light-brown powders. To purify SB-72310 in the powders, column chromatography on DEAE-Sephadex (Pharmacia, Sweden) can be employed with advantage. Thus, a column of DEAE-Saphadex A-25 is washed with M/100 phosphate buffer (pH 6.6) and an aqueous solution of the above powders is passed through the column and adsorbed thereon. The column is washed with the same buffer solution as above and elution is carried out with the buffer containing 0.5 W/V % of sodium chloride. The active fractions are pooled, adjusted to pH 3.0 and passed again through a column of activated charcoal. The column is washed with water and 20 V/V % aqueous methanol successively. Elution is then cairred out with aqueous acetone and after the active fractions are pooled and concentrated under reduced pressure. Acetone is added to the concentrate, whereby SB-72310 is obtained. SB-72310 forms metal salts and ammonium salt. As the metal salts there may be mentioned the sodium salt, potassium salt, lithium salt, etc.

The physico-chemical properties of the SB-72310 obtained in Example 1 which appears hereinafter are as follows.

1. Melting point: Not lower than 110° C.
2. Appearance: White powder
3. Elemental analysis: (after drying under reduced pressure over phosphorus pentoxide at 40° C. for 6 hours) (%):

| C | 34.40 | 34.18 | (34.40 ± 0.5) |
|---|---|---|---|
| H | 5.56 | 5.54 | (5.50 ± 0.5) |
| N | 13.30 | 13.65 | (13.45 ± 0.5) |
| S | 7.56 | 7.75 | (7.75 ± 0.5) |
| (O | 38.90 ± 1.0) | | |

4. Molecular weight:
   Titrometry: 400±20
   Assumed empirical formula (based on the above data):

$C_{12}H_{20}N_4SO_9 \cdot (H_2O)$

Calculated C, 34.78; H, 5.35; N, 13.52, S, 7.74(%)
5. Specific rotation: $[\alpha]_D^{23} +0.5° \pm 5°(c=0.93, H_2O)$
6. Ultraviolet absorption spectrum: End absorptions only (no characteristic absorptions over 210 nm).
7. Infrared absorption spectrum (FIG. 1),
   Dominant peaks (KBr) (cm$^{-1}$): 3440(s), 2920(m), 2850(m), 2600(w), 1770(s), 1650(s), 1530(s), 1458(m), 1390(w), 1340(w), 1280(sh), 1240(s), 1210(sh), 1180(m), 1118(w), 1043(s), 792(w), 632(s) (s, m, w and sh mean strong, medium, weak absorption and shoulder, respectively.)
8. Solubility in solvents:
   Insoluble in petroleum ether, hexane, diethyl ether, benzene, ethyl acetate, chloroform; sparingly soluble in ethanol, pyridine, acetone; soluble in methanol, dimethylsulfoxide; readily soluble in water.
9. Color reactions: Positive ninhydrin, potassium permanganate reactions; negative ferric chloride-potassium ferricyanide, Sakaguchi, Molisch reactions; doubtful positive Ehrlich reaction.
10. Basicity, neutrality or acidity: Acid
11. Nuclear magnetic resonance spectrum: (in dimethylsulfoxide, 100 MHz) δ 3.31 ppm (s, a chemical shift assignable to O-CH$_3$)
12. Stability: Stable in aqueous solution in the range of pH 3 to 7 at 60° C. for 10 minute heating; unstable over pH 8.5.

The physico-chemical properties of the SB-72310 sodium salt obtained in Example 2 which appears hereinafter are as follows.

1. Melting point: Not lower than 110° C.
2. Appearance: White powder
3. Elemental analysis (after drying under reduced pressure over phosphorus pentoxide at 40° C. for 6 hours) (%):

| C | 31.75 | 31.68 |
|---|---|---|
| H | 5.19 | 5.11 |
| N | 12.68 | 12.57 |
| S | 7.16 | 7.10 |
| Na | 5.01 | 4.95 |

4. Molecular weight: Assuming that 1 mol of Na is contained in the molecule.
   Titrometry: 438±5
   Assumed empirical formula (based on the above data):

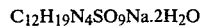

$C_{12}H_{19}N_4SO_9Na \cdot 2H_2O$

Calculated C, 31.72; H, 5.10; N, 12.33; S, 7.06; Na 5.06;
5. Specific rotation: $[\alpha]_D^{23} +8.5° \pm 5°(c=0.91, H_2O)$
6. Ultraviolet absorption spectrum: End absorptions only.
7. Infrared absorption spectrum (FIG. 2),
   Dominant peaks (KBr) (cm$^{-1}$): 3430(s), 3250(sh), 3000(m), 1770(s), 1640(s), 1530(s), 1450(w), 1405(w), 1343(w), 1280(sh), 1245(s), 1180(w), 1118(w), 1050(s), 820(w), 785(w), 632(s). (s, m, w and sh mean strong, medium, weak absorption and shoulder, respectively.)
8. Solubility in solvents: Insoluble in petroleum ether, hexane, diethyl ether, benzene, ethyl acetate, chloroform, acetone; sparingly soluble in methanol, ethanol, pyridine; soluble in dimethylsulfoxide; readily soluble in water.
9. Color reactions: Positive ninhydrin and potassium permanganate reactions; negative ferric chloride-potassium ferricyanide, Sakaguchi and Molisch reactions; doubtful positive Ehrlich reaction.

10. Stability: Stable in aqueous solution in the range of pH 3 to 7 at 60° C. for 10 minute heating; unstable over pH 8.5.

To convert the free acid form of SB-72310 to a salt, the sodium salt, for instance, can be obtained by adding about a molar equivalent of sodium hydroxide to an aqueous solution of the free acid and freeze-drying the system.

To convert a salt of SB-72310 to the free acid form, the latter can be obtained, for example by adding about 1 N-hydrochloric acid to an aqueous solution of the sodium salt, for instance, of SB-72310 to bring the solution to pH 3.0 and desalting the solution by means of activated charcoal.

The biological characteristics of SB-72310 are as follows. The antimicrobial spectra of SB-72310 and its sodium salt against various microorganisms are shown in Table 2.

It will be apparent from this table that Antibiotic SB-72310 is active against gram-positive and gram-negative bacteria.

The acute toxicity of the sodium salt of Antibiotic SB-72310 is low, with no deaths being encountered when 500 mg/kg of the salt was administered to mice by the intravenous route.

TABLE 2

Antimicrobial spectra of SB-72310(Inhibition diameter (mm) by paper disk method) (25 μl of test solution of 10 mg/ml is absorbed in paper disks of 8 mm diameter)

| Test organism | Inhibition diameter(mm) |
|---|---|
| *Pseudomonas fluorescens* IFO 3081 | 12.5 |
| *Escherichia coli* NIHJ JC-2 | 14.5 |
| *Serratia marcescens* IFO 12648 | 17 |
| *Alcaligenes faecalis* IFO 13111 | 23 |
| *Proteus mirabilis* IFO 3849 | 19 |
| *Proteus vulgaris* IFO 3045 | 18 |
| *Salmonella typhimurium* IFO 12529 | 18.5 |
| *Klebsiella pneumoniae* IFO 3318 | 12.5 |
| *Comamonas terrigena* IFD 12685 | 25 |
| *Staphylococcus aureus* FDA 209P | 18.5 |
| *Sarcina lutea* IFO 3232 | 23 |
| *Bacillus subtilis* IFO 3513 | 22 |
| *Bacillus cereus* IFO 3466 | 14.5 |

Note:
Medium = Trypticase-soy-broth-agar

As will be seen from the above antimicrobial spectrum, SB-72310 according to this invention is inhibitory to gram-negative and gram-positive bacteria. Therefore, it can be used in the treatment of infections with the above-mentioned bacteria in mammalian animals (e.g. mouse, rat, dog and man) and domesticated avian species (e.g. fowl and duck).

To use SB-72310 as a remedy of *Escherichia coli* infections, it is dissolved in physiological saline, for instance, and parenterally administered, e.g. subcutaneously or intramuscularly, at the dose level of 15 to 60 mg/kg body weight daily.

For oral use, Antibiotic SB-72310 is admixed with lactose, for instance, encapsulated and administered at the dose level of 60 to 400 mg (as SB-72310)/kg body weight daily.

SB-72310 may also be used as a germicide or disinfectant. For instance, SB-72310 is dissolved in distilled water to prepare a solution containing 0.1 to 1.0 W/V percent of SB-72310 or formulated with an ointment basis such as vaseline or lanolin to prepare an ointment containing 15 to 60 mg of SB-72310 per gram and said solution or ointment is applied to the paws, legs, eyes, ears or other parts of the above-mentioned animals as a disinfectant.

SB-72310 is a very promising compound in that it is useful as an intermediate for the synthesis of new medical substances.

Comparison of Antibiotic SB-72310 with the known antibiotics has revealed the following. First, as antibiotics which are soluble in water and acidic and contain sulfur, there may be mentioned penicillins and cephalosporins. However, in that SB-72310 does not absorb in the ultraviolet region of the spectrum, it differentiates itself from cephalosporins. Moreover, the fact that the nuclear magnetic resonance spectrum gives a chemical shift assignable to O-methyl protons and the fact that it gives rise to glutamic acid on acid hydrolysis are the lines of evidence that SB-72310 is different from any of the naturally-occurring penicillins and cephalosporins.

On the other hand, there are many known antibiotics elaborated by bacteria of the genus Pseudomonas but none of them is a water-soluble antibiotic which is acidic and contains sulfur. Moreover, SB-72310 is dissimilar to any of the known antibiotics produced by microorganisms other than Pseudomonas strains in view of its unique physicochemical and biological properties.

Antibiotic G-6302 has been obtained by means of cultivation of a microorganism belonging to the genus Psuedomonas in a culture medium and recovery from the cultured broth by one of the present inventors together with two other inventors.

Antibiotic G-6302 and the present Antibiotic SB-72310 are indistinguishable from one another in molecular formula, infrared absorption spectra, nuclear magnetic resonance spectra, color reactions, stability, etc. But they are clearly distinguishable, in particular, in specific rotation in that the value of $[\alpha]_D^{23}$ of free form of Antibiotic G-6302 is $+94°\pm10°(c=0.35, H_2O)$, whereas that of free form of Antibiotic SB-72310 is $+0.5°\pm5°(c=0.93, H_2O)$.

Thus, it is considered that the present Antibiotic SB-72310 is different from Antibiotic G-6302.

From the aforementioned facts, it is concluded that SB-72310 is a novel compound.

The following examples are further illustrative of this invention.

In the examples, "part(s)" is based on weight unless otherwise noted and the relationship between "part(s)" and "part(s) by volume" corresponds to that between "gram(s)" and "milliliter(s)", and "%" is based on "weight/volume" unless otherwise noted.

EXAMPLE 1

The cells of *Pseudomonas mesoacidophila* SB-72310 (FERM receipt number 4653; IFO 13884; ATCC-31433) grown on a nutrient agar slant were used to inoculate two $2\times10^3$ parts by volume Sakaguchi flasks each containing 500 parts by volume of a medium composed of 1% glucose, 0.5% Polypepton (prepared by Daigo Nutritive Chemicals Co., Japan), 0.5% meat extract, 0.5% sodium chloride (pH 7.0) and each flask was incubated on a reciprocating shaker at 28° C. for 48 hours. The resultant culture was used as a seed culture.

A $200\times10^3$ parts by volume stainless steel tank fermentor was filled with $120\times10^3$ parts by volume of a medium composed of 1.5% sucrose, 0.3% yeast extract, 0.2% ammonium sulfate, 0.6% potassium dihydrogen phosphate, 0.3% dipotassium hydrogen phosphate, 0.05% magnesium sulfate, 0.05% NaCl and sterilized with steam at 120° C. for 20 minutes. The sterilized tank was then inoculated with the above seed culture and incubated at a temperature of 28° C. with aeration at the rate of $120 \times 10^3$ parts by volume/min. and at 180 r.p.m. agitation for 78 hours. The resultant broth was centrifuged with a Sharpless centrifugal separator to remove the cells, which left $110 \times 10^3$ parts by volume of supernatant fluid. The fluid was adjusted to pH 4.2 and passed through a column of $15 \times 10^3$ parts by volume of activated charcoal (chromatographic Grade SHIRASAGI, manufactured by Takeda Chemical Industries, Ltd., Japan) to have active substance adsorbed thereon. The column was rinsed with $45 \times 10^3$ parts by volume of water and, then, elution was carried out with $45 \times 10^3$ parts by volume of 50 V/V % aqueous acetone, the eluate being collected in $10 \times 10^3$ parts by volume fractions. The fractions were assayed against *Comamonas terrigena* IFO 12685. The fractions Nos. 2 and 3 were pooled, $20 \times 10^3$ parts by volume of water was added and the mixture was passed through a column packed with $10 \times 10^3$ parts by volum of Dowex-1 (Cl-form) (Dow and Chemical Industries, U.S.A.). The column was rinsed with $25 \times 10^3$ parts by volume of water and elution was carried out with $50 \times 10^3$ parts by volume of a 5% aqueous sodium chloride solution. The active fractions were pooled, adjusted to pH 4.0 and passed again through a column of activated charcoal ($8 \times 10^3$ parts by volume). The column was washed with $24 \times 10^3$ parts by volume of water and elution was carried out with 20 V/V % aqueus methanol. The active fractions were pooled and concentrated to 50 parts by volume under reduced pressure. Then, 200 parts by volume of acetone was added and the resultant precipitate was recovered by filtration, washed with 50 parts by volume of acetone and 100 parts by volume of diethyl ether, followed by drying under reduced pressure. By the above procedure there was obtained 12 parts of crude product.

In 500 parts by volume of M/100 phosphate buffer (pH 6.6) was dissolved 10 parts of the above crude product and the solution was passed through a column of 200 parts by volume of DEAE-Sephadex A-25 (Pharmacia, Sweden previously buffered with the same buffer solution as mentioned. The column was washed with 400 parts by volume of the same buffer solution and, then, elution was carried out with the same buffer to which 0.5% of sodium chloride had been added. The active fractions were pooled, adjusted to pH 3.2 with 1N-HCl and passed through a column of 60 parts by volume of activated charcoal. The column was washed with 200 parts by volume of water and 100 parts by volume of 20 V/V % aqueous methanol, followed by eluting with 50 V/V % aqueous acetone. The active fractions were pooled, concentrated under reduced pressure and dissolved in 5 parts by volume of methanol. Following addition of 100 parts by volume of acetone, the solution was allowed to stand in the cold. The resultant precipitate was recovered by filtration, washed with diethyl ether and dried under reduced pressure and over phosphorus pentoxide at 40° C. for 6 hours. By the above procedure there was obtained 3.8 parts of powders. The infrared absorption spectrum of this product is shown in FIG. 1.

Elemental analysis: C, 34.40; H, 5.56; N, 13.30; S, 7.56 (W/W %).

EXAMPLE 2

Figure 2:
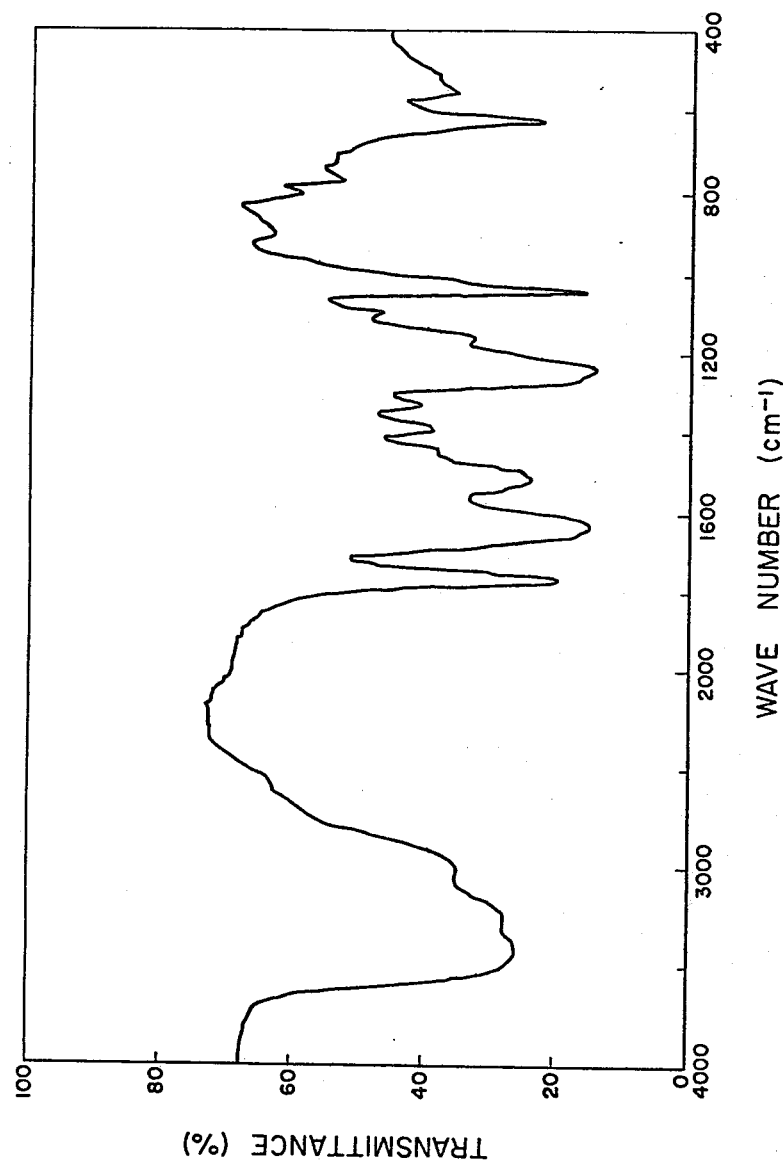

In 45 parts by volume of water was dissolved 2.0 parts of the free acid of SB-73210 obtained in Example 1, and under cooling, about 4.5 parts by volume of 1 N-aqueous sodium hydroxide was added. This was followed by the addition of a further amount of 1 N-sodium hydroxide with the pH of the solution being monitored until the pH of 6.5 was established. The solution was freeze-dried, whereby 2.1 parts of SB-72310 monosodium salt was obtained as white powders. The infrared absorption spectrum of this product after drying under reduced pressure and at 40° C. for 6 hours is shown in FIG. 2.

Elemental analysis: C, 31.75; H, 5.19; N, 12.68; S, 7.16; Na, 5.01 (W/W %).

EXAMPLE 3

The cells of *Pseudomonas mesoacidophila* SB-72310 (FERM receipt number 4653; IFO 13884; ATCC-31433) grown on a nutrient agar slant were used to inoculate a 200 parts by volume conical flask containing 40 parts by volume of a medium composed of 3% glycerol, 0.1% glucose, 0.5% Polypepton, 0.5% meat extract and 0.5% sodium chloride (pH 6.5) and the inoculated flask was incubated on a rotary shaker at 28° C. for 48 hours to prepare a seed culture.

Then, 200 parts by volume conical flasks were each filled with 40 parts by volume of a medium similar to the above containing various sulfur compounds.

Each flask was then inoculated with 1 part by volume of the above seed culture and incubated on a rotary shaker at 28° C. for 96 hours. As will be apparent from the following table, the production of SB-72310 was markedly increased by the addition of sulfur compounds.

TABLE 3

| | Production amount of SB-82310 | |
|---|---|---|
| Compound added | Concentration (W/V %) | Production Amount (μg/ml) |
| None | — | 21 |
| Ammonium sulfate | 0.25 | 47 |
| Ammonium sulfite | 0.25 | 68 |
| Ammonium thiosulfate | 0.25 | 90 |
| Cysteine | 0.25 | 54 |
| Cystine | 0.25 | 68 |
| L-Thiazolicine-4-carboxylic acid | 0.25 | 90 |
| Hypotaurine | 0.25 | 47 |
| Glutathione | 0.25 | 38 |

What we claim is:

1. A member selected from the group consisting of antibiotic SB-72310 having the following characteristics, and a sodium, potassium, lithium or ammonium salt thereof:

(1) Melting point: Not lower than 110° C.
(2) Appearance: White powder
(3) Elemental analysis: (%)

| | |
|---|---|
| C | 34.40 ± 0.5 |
| H | 5.50 ± 0.5 |
| N | 13.30 ± 0.5 |
| O | 38.90 ± 1.0 |
| S | 7.75 ± 0.5 |

(as dried at 40° C. for 6 hours over phosphorus pentoxide under reduced pressure)

(4) Molecular weight: 400±20 (by titrometry)
(5) Specific rotation: $[\alpha]_D^{23} +0.5° ±5°$ (c=0.93, $H_2O$)
(6) Ultraviolet absorption spectrum: No characteristic absorption over 210 nm
(7) Infrared absorption spectrum [dominant peaks (KBr) (cm$^{-1}$)]: 1770, 1650, 1530, 1240, 1043
(8) Solubility:
Insoluble in petroleum ether, hexane, diethyl ether, benzene, ethyl acetate, chloroform; sparingly soluble in ethanol, pyridine, acetone; soluble in methanol, dimethylsulfoxide; readily soluble in water
(9) Color reactions:
Positive ninhydrin, potassium permanganate reactions; negative ferric chloride-potassium ferricyanide, Sakaguchi, Molisch reactions; doubtful positive Ehrlich reaction
(10) Basicity, neutrality or acidity: Acid.

2. A method for producing Antibiotic SB-72310 as defined in claim 1 comprising cultivating a microorganism having the characteristics of *Pseudomonas mesoacidophila* SB-72310 (ATCC 31433) in a culture medium containing an assimilable carbon source and a digestible nitrogen source under aerobic conditions at pH 4 to 8 and at a temperature in the range of 15° to 35° C. until Antibiotic SB-72310 is substantially elaborated and accumulated in the cultured broth and recovering Antibiotic SB-72310 therefrom.

3. A method as claimed in claim 2, wherein the culture medium is supplemented with 0.01 to 1.0 w/v% of a sulfur compound which is assimilated by the microorganism and which is selected from the group consisting of ammonium sulfate, ammonium sulfite, ammonium thiosulfate, cysteine, cystine, L-thiazolidine-4-carboxylic acid, hypotaurine and glutathione.

* * * * *